(12) United States Patent
Milliman

(10) Patent No.: US 9,393,014 B2
(45) Date of Patent: Jul. 19, 2016

(54) SURGICAL INSTRUMENT WITH INDICATOR

(71) Applicant: Covidien LP, Mansfield, MA (US)

(72) Inventor: Keith L. Milliman, Bethel, CT (US)

(73) Assignee: COVIDIEN LP, Mansfield, MA (US)

( * ) Notice: Subject to any disclaimer, the term of this patent is extended or adjusted under 35 U.S.C. 154(b) by 667 days.

(21) Appl. No.: 13/827,211

(22) Filed: Mar. 14, 2013

(65) Prior Publication Data

US 2013/0193187 A1 Aug. 1, 2013

Related U.S. Application Data

(63) Continuation of application No. 13/537,216, filed on Jun. 29, 2012, now Pat. No. 8,418,905, which is a continuation of application No. 13/274,811, filed on Oct. 17, 2011, now Pat. No. 8,215,530, which is a (Continued)

(51) Int. Cl.
*A61B 17/068* (2006.01)
*A61B 17/115* (2006.01)
(Continued)

(52) U.S. Cl.
CPC ............. *A61B 17/068* (2013.01); *A61B 17/115* (2013.01); *A61B 2017/00128* (2013.01); *A61B 2017/00367* (2013.01); *A61B 2017/0725* (2013.01)

(58) Field of Classification Search
CPC .................. A61B 2019/448; A61B 2019/4836; A61B 2019/4857; A61B 2017/00115; A61B 2017/00128; A61B 2017/00022; A61B 2017/00212; A61B 19/5244; A61B 17/068; A61B 2017/0725; A61B 17/1155
USPC ............................... 227/175.1, 175.2; 606/75
See application file for complete search history.

(56) References Cited

U.S. PATENT DOCUMENTS 4,379,457 A 4/1983 Gravener et al.
4,527,724 A * 7/1985 Chow .................. A61B 17/072
227/19

(Continued)

FOREIGN PATENT DOCUMENTS

EP 1 813 206 A1 8/2007
EP 1997438 12/2008
(Continued)

OTHER PUBLICATIONS

European Search Report dated Jul. 16, 2013 in copending European Application No. 09252120.

(Continued)

*Primary Examiner* — Gloria R Weeks
*Assistant Examiner* — Justin Citrin

(57) ABSTRACT

A surgical stapling instrument including a handle assembly, an elongated body portion extending distally from the handle assembly, a head portion and an indicator. A firing trigger is movable between first and second positions. The head portion includes an anvil assembly and a shell assembly. The anvil assembly is movable in relation to the shell assembly between spaced and approximated positions. The indicator is disposed in mechanical cooperation with the handle assembly and is movable between a first position and a second position in response to movement of the anvil assembly towards its approximated position. The indicator is movable between the second position and a third position in response to firing of the instrument.

20 Claims, 10 Drawing Sheets

Related U.S. Application Data continuation of application No. 12/546,899, filed on Aug. 25, 2009, now Pat. No. 8,113,405.

(60) Provisional application No. 61/093,751, filed on Sep. 3, 2008.

(51) Int. Cl.
*A61B 17/072* (2006.01)
*A61B 17/00* (2006.01)

(56) References Cited

U.S. PATENT DOCUMENTS

| | | | |
|---|---|---|---|
| 4,892,244 A | 1/1990 | Fox et al. | |
| 5,005,749 A * | 4/1991 | Aranyi | A61B 17/115 227/175.1 |
| 5,071,052 A | 12/1991 | Rodak et al. | |
| 5,258,007 A | 11/1993 | Spetzler et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A * | 8/1994 | Main | A61B 17/115 227/179.1 |
| 5,350,104 A | 9/1994 | Main et al. | |
| 5,403,312 A | 4/1995 | Yates et al. | |
| 5,443,198 A * | 8/1995 | Viola | A61B 17/072 227/175.1 |
| 5,464,144 A * | 11/1995 | Guy | A61B 17/072 128/104.1 |
| 5,474,223 A | 12/1995 | Viola et al. | |
| 5,529,235 A | 6/1996 | Boiarski et al. | |
| 5,533,661 A | 7/1996 | Main et al. | |
| 5,535,934 A | 7/1996 | Boiarski et al. | |
| 5,535,937 A | 7/1996 | Boiarski et al. | |
| 5,607,436 A | 3/1997 | Pratt et al. | |
| 5,685,474 A * | 11/1997 | Seeber | A61B 17/115 227/175.1 |
| 5,688,270 A | 11/1997 | Yates et al. | |
| 5,697,543 A | 12/1997 | Burdorff | |
| 5,709,680 A | 1/1998 | Yates et al. | |
| 5,762,255 A | 6/1998 | Chrisman et al. | |
| 5,797,537 A | 8/1998 | Oberlin et al. | |
| 5,799,857 A | 9/1998 | Robertson et al. | |
| 5,807,393 A | 9/1998 | Williamson, IV et al. | |
| 5,810,811 A | 9/1998 | Yates et al. | |
| 5,820,009 A | 10/1998 | Melling et al. | |
| 5,833,690 A | 11/1998 | Yates et al. | |
| 5,882,340 A | 3/1999 | Yoon | |
| 5,915,616 A | 6/1999 | Viola et al. | |
| 6,010,054 A | 1/2000 | Johnson et al. | |
| 6,024,741 A | 2/2000 | Williamson, IV et al. | |
| 6,050,472 A | 4/2000 | Shibata | |
| 6,066,145 A | 5/2000 | Wurster | |
| H1904 H | 10/2000 | Yates et al. | |
| 6,269,997 B1 | 8/2001 | Balazs et al. | |
| 6,601,748 B1 | 8/2003 | Fung et al. | |
| 6,769,594 B2 | 8/2004 | Orban, III | |
| 6,945,444 B2 * | 9/2005 | Gresham | A61B 17/115 227/175.1 |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,159,750 B2 | 1/2007 | Racenet et al. | |
| 7,168,604 B2 * | 1/2007 | Milliman | A61B 17/1114 227/175.1 |
| 7,234,624 B2 * | 6/2007 | Gresham | A61B 17/115 227/175.1 |
| 7,237,708 B1 | 7/2007 | Guy et al. | |
| 7,303,106 B2 * | 12/2007 | Milliman | A61B 17/115 227/175.1 |
| 7,364,060 B2 | 4/2008 | Milliman | |
| 7,364,061 B2 * | 4/2008 | Swayze | A61B 17/07207 227/175.1 |
| 7,556,186 B2 | 7/2009 | Milliman | |
| 7,784,663 B2 | 8/2010 | Shelton, IV | |
| 7,866,527 B2 | 1/2011 | Hall et al. | |
| 7,886,951 B2 | 2/2011 | Hessler | |
| 8,113,405 B2 | 2/2012 | Milliman | |
| 8,215,530 B2 | 7/2012 | Milliman | |
| 8,418,905 B2 | 4/2013 | Milliman | |
| 2005/0006432 A1 | 1/2005 | Racenet et al. | |
| 2005/0006433 A1 | 1/2005 | Milliman et al. | |
| 2005/0067457 A1 | 3/2005 | Shelton et al. | |
| 2005/0067458 A1 * | 3/2005 | Swayze | A61B 17/07207 227/176.1 |
| 2005/0103819 A1 | 5/2005 | Racenet et al. | |
| 2005/0116009 A1 * | 6/2005 | Milliman | A61B 17/068 227/176.1 |
| 2005/0205640 A1 | 9/2005 | Milliman | |
| 2006/0025816 A1 | 2/2006 | Shelton | |
| 2006/0097025 A1 | 5/2006 | Milliman et al. | |
| 2006/0097026 A1 | 5/2006 | Shelton et al. | |
| 2006/0175375 A1 | 8/2006 | Shelton et al. | |
| 2006/0201992 A1 | 9/2006 | Racenet et al. | |
| 2006/0212069 A1 | 9/2006 | Shelton | |
| 2006/0219752 A1 | 10/2006 | Arad et al. | |
| 2006/0235437 A1 | 10/2006 | Vitali et al. | |
| 2006/0235438 A1 | 10/2006 | Huitema et al. | |
| 2006/0235439 A1 | 10/2006 | Molitor et al. | |
| 2006/0235440 A1 | 10/2006 | Huitema et al. | |
| 2006/0235441 A1 | 10/2006 | Huitema et al. | |
| 2006/0235442 A1 | 10/2006 | Huitema | |
| 2006/0235443 A1 | 10/2006 | Huitema et al. | |
| 2006/0235444 A1 | 10/2006 | Huitema et al. | |
| 2006/0271094 A1 | 11/2006 | Hudson et al. | |
| 2006/0273135 A1 * | 12/2006 | Beetel | A61B 17/068 227/175.1 |
| 2006/0278680 A1 * | 12/2006 | Viola | A61B 17/07207 227/176.1 |
| 2007/0034670 A1 | 2/2007 | Racenet et al. | |
| 2007/0049950 A1 | 3/2007 | Theroux et al. | |
| 2007/0060952 A1 * | 3/2007 | Roby | A61B 17/115 606/219 |
| 2007/0075117 A1 | 4/2007 | Milliman et al. | |
| 2007/0108252 A1 | 5/2007 | Racenet et al. | |
| 2007/0175964 A1 | 8/2007 | Shelton et al. | |
| 2007/0191868 A1 * | 8/2007 | Theroux | A61B 17/1285 606/142 |
| 2008/0237298 A1 * | 10/2008 | Schall | A61B 17/07207 227/180.1 |
| 2008/0312687 A1 | 12/2008 | Blier | |

FOREIGN PATENT DOCUMENTS

| | | |
|---|---|---|
| EP | 2 090 255 A1 | 8/2009 |
| WO | WO-98/30153 A1 | 7/1998 |

OTHER PUBLICATIONS

European Search Report from corresponding European Application No. EP 10 25 1306 date of completion Dec. 2, 2010.

* cited by examiner

SURGICAL INSTRUMENT WITH INDICATOR

CROSS-REFERENCE TO RELATED APPLICATIONS

The present application claims the benefits of, priority to, and is a Continuation of U.S. patent application Ser. No. 13/537,216, filed on Jun. 29, 2012, which claims the benefits of, priority to, and is a Continuation of U.S. Pat. No. 8,215,530, issued on Jul. 10, 2012, which claims the benefits of, priority to, and is a Continuation of U.S. Pat. No. 8,113,405, issued on Feb. 14, 2012, which claims the benefits of and priority to Provisional Patent Application Ser. No. 61/093,751, filed on Sep. 3, 2008, the entire contents of each of which are incorporated herein by reference.

BACKGROUND

1. Technical Field

The present disclosure relates generally to a surgical stapling instrument for applying surgical staples to body tissue. More particularly, the present disclosure relates to a surgical stapling instrument with an approximation and firing indicator.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described for example in U.S. Pat. Nos. 7,303,106, 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component as these components are approximated. The clamped tissue is stapled by driving one or more staples from the staple holding component so that the ends of the staples pass through the tissue and are deformed by the anvil head. An annular knife is concurrently advanced to core tissue within the hollow organ to free a tubular passage within the organ.

Besides anastomosis of hollow organs, surgical stapling instruments for performing circular anastomosis have been used to treat internal hemorrhoids in the rectum. Typically, during use of a circular stapling instrument for hemorrhoid treatment, the anvil head and the staple holding component of the surgical stapling instrument are inserted through the anus and into the rectum with the anvil head and the staple holding component in an open or unapproximated position. Thereafter, a pursestring suture is used to pull the internal hemorrhoidal tissue towards the anvil rod. Next, the anvil head and the staple holding component are approximated to clamp the hemorrhoid tissue between the anvil head and the staple holding component. The stapling instrument is fired to remove the hemorrhoidal tissue and staple the cut tissue. In stapled hemorrhoidopexy, a strip of mucosa and submucosa at the top of the hemorrhoids is removed by the stapling instrument, thereby treating the hemorrhoids by inhibiting blood flow to the tissue.

In certain situations, it is desirable to provide an indication to the user regarding the approximation and firing status of the instrument. Accordingly, it would be desirable for a surgical instrument to include an indicator to let the user know when the instrument has been approximated and when the instrument has been fired.

SUMMARY

The present disclosure relates to a surgical stapling instrument including a handle assembly, an elongated body portion extending distally from the handle assembly, a head portion and an indicator. The handle assembly includes a firing trigger. The firing trigger is movable between a first non-actuated position and a second actuated position. The head portion is disposed adjacent a distal portion of the elongated body portion and includes an anvil assembly and a shell assembly. The anvil assembly is movable in relation to the shell assembly between spaced and approximated positions. The indicator is disposed in mechanical cooperation with the handle assembly and is movable between a first position and a second position in response to movement of the anvil assembly towards its approximated position. The indicator is movable between the second position and a third position in response to the firing of the instrument.

In one embodiment, the handle assembly includes a pawl and the firing trigger is configured to contact the pawl when the firing trigger is moved to the second actuated position. The indicator can include a first indicia visible to a user when the indicator is in its second position and a second indicia visible to the user when the indicator is in its third position. Preferably the indicator is rotatable with respect to a stationary handle of the handle assembly. The indicator is preferably biased toward its first position and preferably rotatable in a first direction from its first position toward its second position and from its second position towards its third position. The pawl is preferably rotatable relative to the stationary handle in a second direction opposite the first direction.

In one embodiment, the handle assembly includes a rotatable member operatively associated with the indicator and the firing trigger has an engagement surface, the engagement surface effecting rotation of the indicator to the third position to rotate the rotatable member upon movement of the firing trigger to the second actuated position. A slide member can be provided operatively associated with the indicator and a pawl has a rib engageable with the slide member.

A lockout mechanism could be provided disposed in mechanical cooperation with the handle assembly, wherein approximation of the anvil assembly causes the lockout mechanism to move from a blocking position, wherein the firing trigger is prevented from moving towards the stationary handle, to an enabling position, wherein the firing trigger is capable of moving towards the stationary handle.

In another aspect, the present disclosure relates to a method of performing a surgical procedure. The method includes providing a surgical instrument including a handle assembly, an elongated body portion extending distally from the handle assembly, a head portion and an indicator. The handle assembly includes a firing trigger, which is movable between a first non-actuated position and a second actuated position. The head portion is disposed adjacent a distal portion of the elongated body portion and includes an anvil assembly and a shell assembly. The anvil assembly is movable in relation to the shell assembly between spaced and approximated positions. The indicator is disposed in mechanical cooperation with the handle assembly. The method also includes the steps of positioning the surgical instrument adjacent a surgical site, rotating an approximation mechanism to move the anvil assembly towards its approximated position to affect rotation of the indicator from a first position to a second position, and subsequently moving the firing trigger through a complete firing stroke to affect rotation of the indicator from the second to a third position.

In a preferred embodiment, the step of moving the firing trigger through a complete firing stroke causes the firing trigger to contact a pawl upon completion of the firing stroke and the pawl is disposed in mechanical cooperation with the indicator to effect rotation of the indicator.

Preferably, the indicator includes at least two different indicia including a first indicia being visible to a user when the indicator is rotated to its second position and a second indicia being visible to the user when the indicator is rotated to its third position.

Preferably, the indicator is rotatable in a first direction from its first position towards its second position and from its second position towards its third position, and the pawl is rotatable relative to the stationary handle in a second direction, the second direction being opposite the first direction. The indicator can be biased toward its first position.

DESCRIPTION OF THE DRAWINGS

Various embodiments of the presently disclosed surgical stapling instrument are disclosed herein with reference to the drawings, wherein.

DETAILED DESCRIPTION OF EMBODIMENTS

Figure 1:
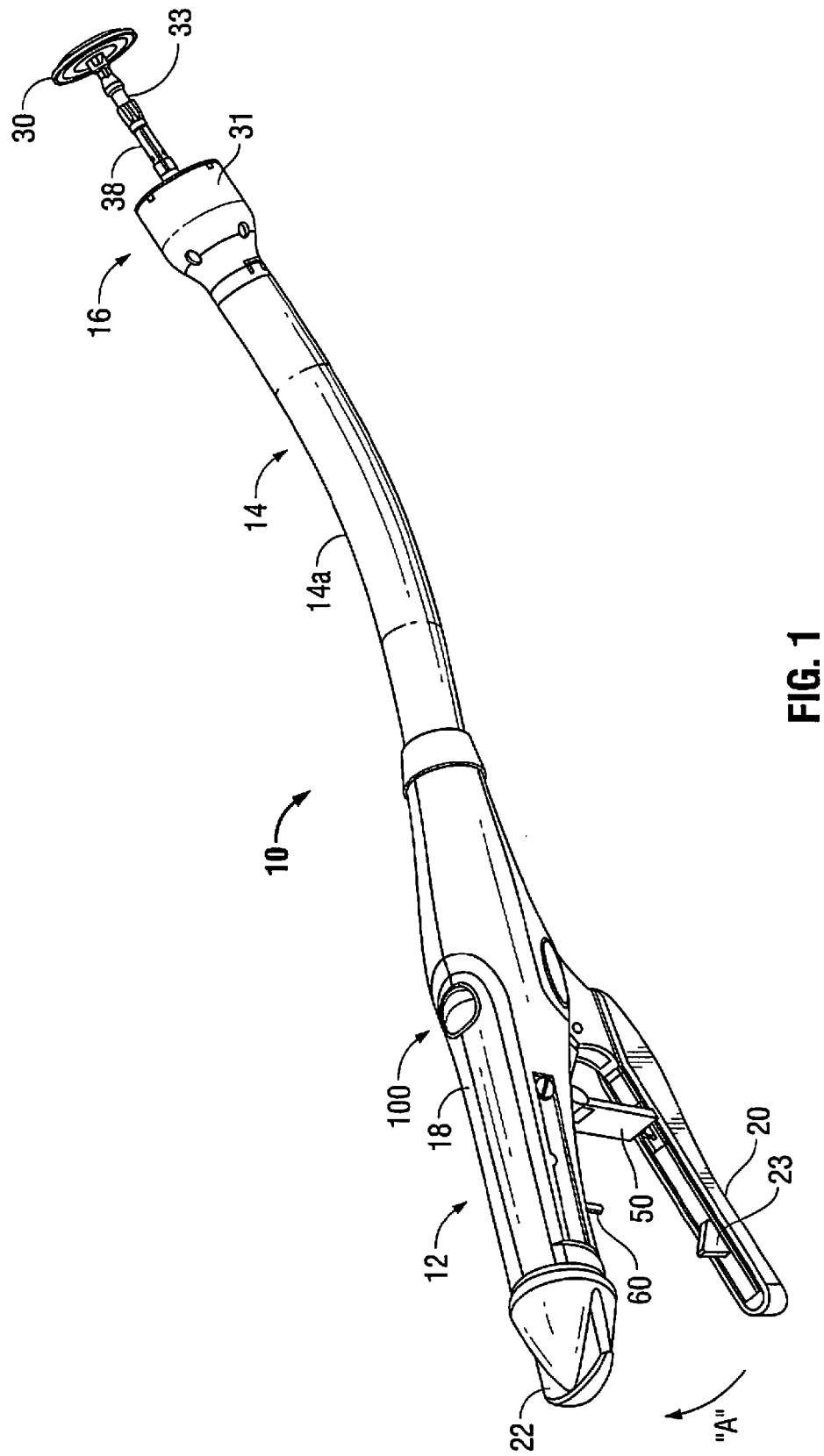
FIG. 1 is a perspective view of the presently disclosed surgical stapling instrument illustrated in an unapproximated position, in accordance with an embodiment of the present disclosure.

Embodiments of the presently disclosed surgical stapling instrument will now be described in detail with reference to the drawings in which like reference numerals designate identical or corresponding elements in each of the several views.

Throughout this description, the term "proximal" will refer to the portion of the instrument closer to the operator and the term "distal" will refer to the portion of the instrument further from the operator.

Figure 2:
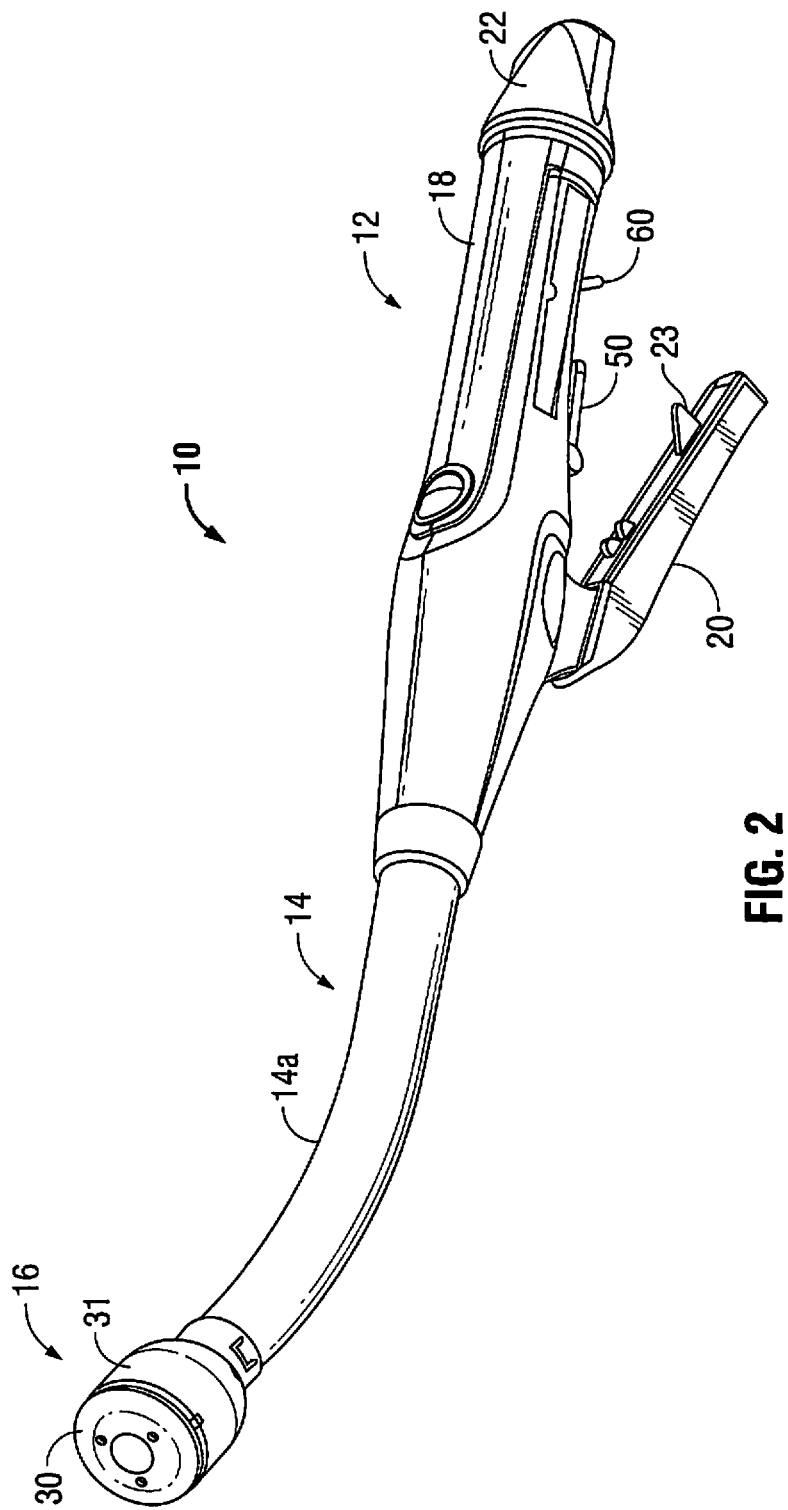
FIG. 2 is a perspective view of the surgical stapling instrument of FIG. 1 illustrated in an approximated unfired position.
Figure 3:
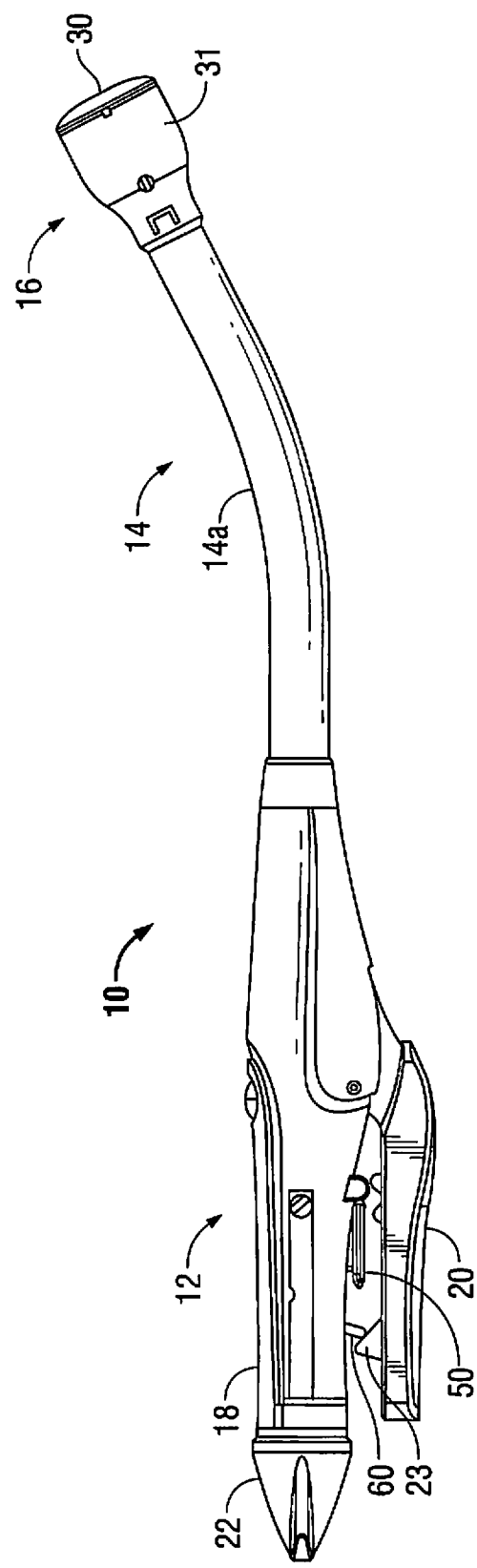
FIG. 3 is a perspective view of the surgical stapling instrument of FIG. 1 illustrated in a fired position.

FIGS. 1-3 illustrate one embodiment of the presently disclosed surgical stapling instrument shown generally as 10. Briefly, surgical stapling instrument 10 includes a handle assembly 12, an elongated body portion 14 including a curved elongated outer tube 14a, and a head portion 16. Alternately, in some surgical procedures, e.g., the treatment of hemorrhoids, it is desirable to have a substantially straight body portion. The length, shape and/or the diameter of body portion 14 and head portion 16 may also be varied to suit a particular surgical procedure.

With continued reference to FIGS. 1-3, handle assembly 12 includes a stationary handle 18, a firing trigger 20, a rotatable approximation knob 22 and an indicator mechanism 100. Head portion 16 includes an anvil assembly 30 and a shell assembly 31. Anvil assembly 30 is movable in relation to shell assembly 31 between spaced and approximated positions.

With continued reference to FIGS. 1-3, in operation, rotation of approximation knob 22 causes movement of anvil assembly 30 in relation to shell assembly 31 between spaced (FIG. 1) and approximated (FIG. 2) positions, as approximation knob 22 is operably associated with anvil retainer 38 (FIG. 1), which is connected to the anvil shaft or center rod 33 of anvil assembly 30. Rotation of approximation knob 22 in a first direction (e.g., clockwise) causes proximal movement of anvil assembly 30 by retracting anvil retainer 38, and rotation of approximation knob 22 in a second opposite direction (e.g., counter-clockwise) causes distal movement of anvil assembly 30 as anvil retainer is advanced distally. Other approximation mechanisms are also contemplated.

Figure 4:
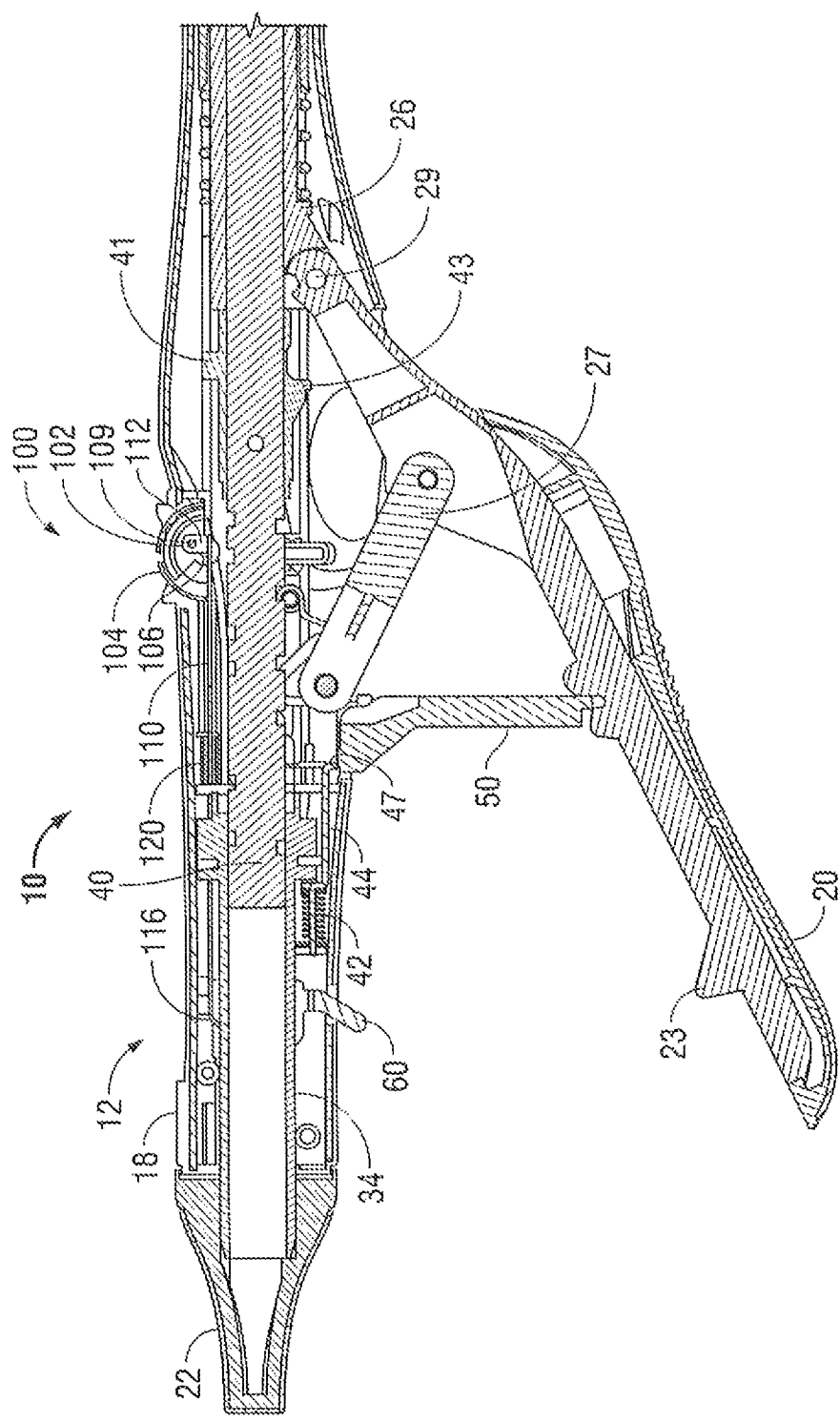
FIG. 4 is a longitudinal, cross-sectional view of a portion of the surgical stapling instrument in the unapproximated position, as illustrated in FIG. 1.
Figure 4A:
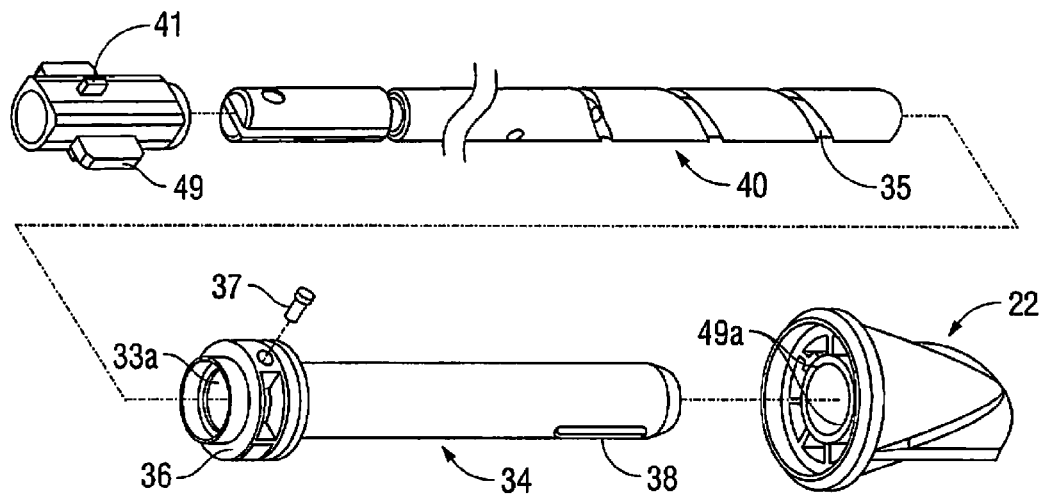
FIG. 4A is an exploded perspective view of a portion of the approximation mechanism.
Figure 5:
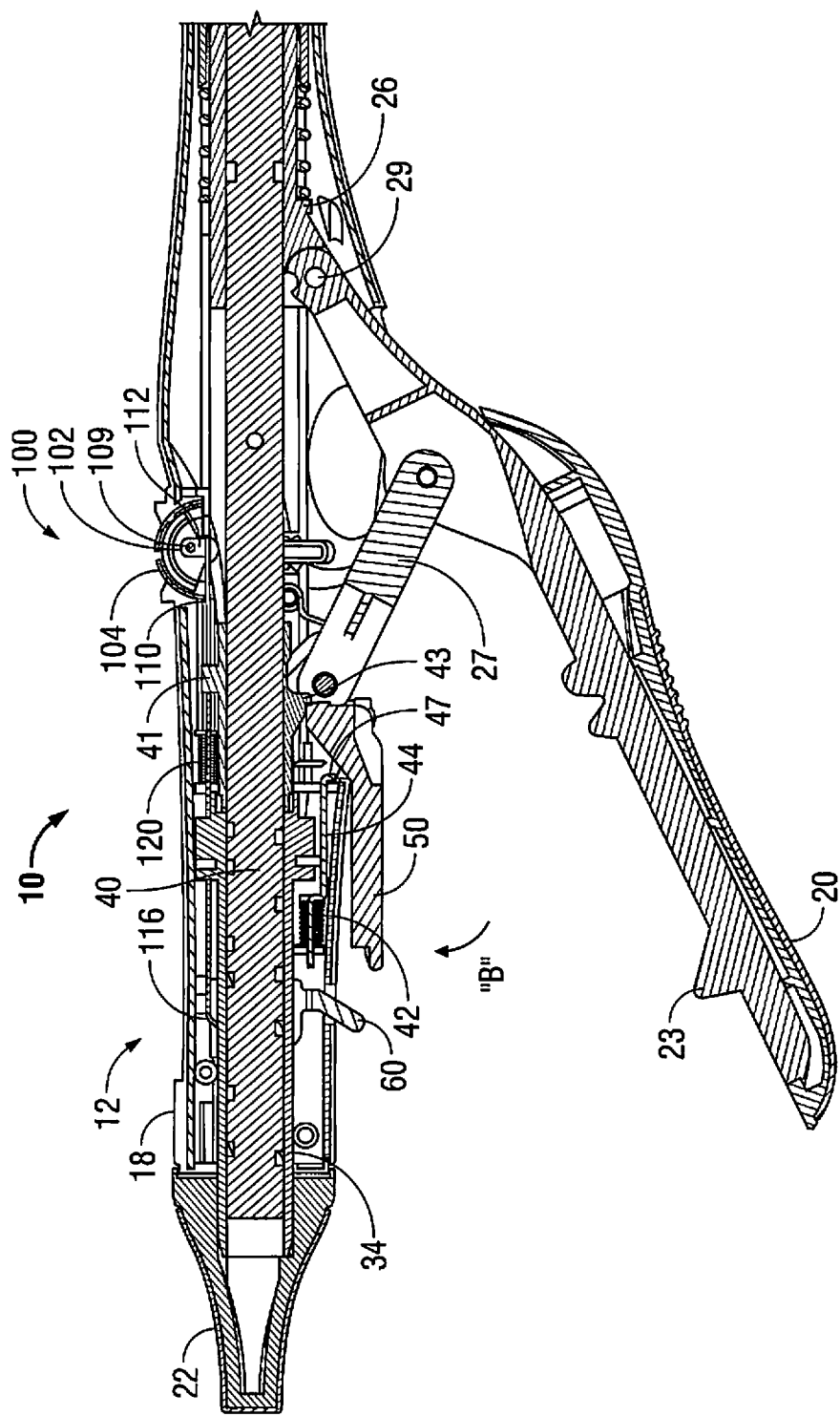
FIG. 5 is a longitudinal, cross-sectional view of a portion of the surgical stapling instrument in the approximated unfired position, as illustrated in FIG. 2.
Figure 6:
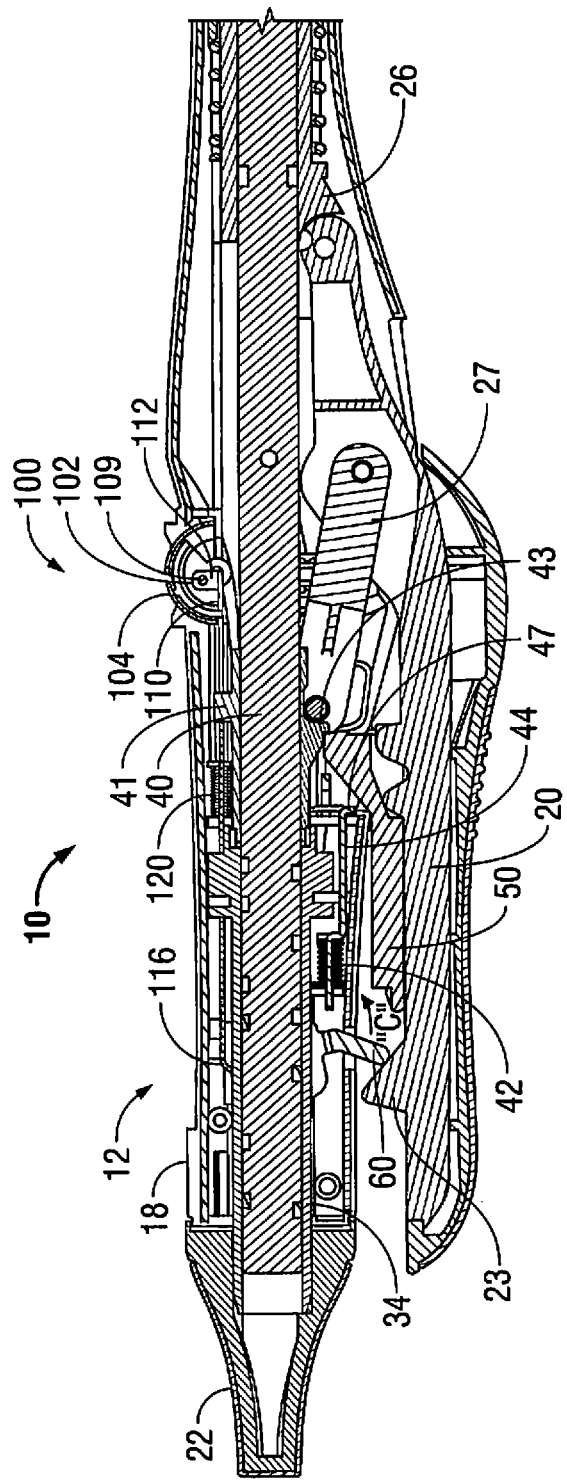
FIG. 6 is a longitudinal, cross-sectional view of the surgical stapling instrument in the fired position, as illustrated in FIG. 3.

Referring now to FIGS. 4-6, more specifically, approximation knob 22 is mechanically engaged with a screw 40 and screw 40 is in mechanical cooperation with anvil retainer 38 which is engaged with anvil assembly 30. As shown in FIG. 4A, the proximal portion of screw 40 has a helical channel 35 and is slidably positioned within central bore 33a of rotatable sleeve 34. The proximal portion of sleeve 33 extends through an opening in the proximal end of the stationary handle 18 and elongated ribs 39 on its outer surface are received in internal slots 49a of rotation knob 22 to fix sleeve 34 to knob 22. A pin 37 extends through cylindrical collar 36 of sleeve 34 into helical channel 35. Since sleeve 33 is axially fixed with respect to stationary handle 18, rotation of sleeve 34 about screw 40 causes pin 37 to move along channel 35 of screw 40 to effect axial movement of screw 40. Further details of the approximation mechanism are described in U.S. Pat. No. 7,303,106, the entire contents of which are incorporated herein by reference. Rotation of approximation knob 22 in the first direction causes screw 40 to move proximally, which in turn causes proximal movement of anvil retainer 38 and anvil assembly 30 to approximate the anvil toward the fasteners.

FIGS. 4, 5 and 6 show a lockout mechanism including a trigger lock 50. Trigger lock 50 is disposed in mechanical cooperation with handle assembly 12 and maintains firing trigger 20 in an open inactivated position until anvil assembly 30 and shell assembly 31 have been approximated. With the trigger lock 50 in the blocking position shown in FIG. 4, wherein the anvil is in an unapproximated (spaced) position, firing trigger 20 cannot be squeezed. As can be appreciated, the lockout mechanism therefore helps prevent staples from being fired prematurely, i.e., before approximation of the anvil assembly, by blocking movement of the firing trigger 30.

Figure 6A:
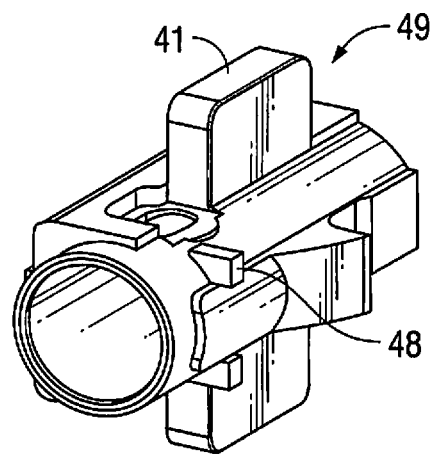
FIG. 6A is a perspective view of the screw stop of the approximation mechanism.
Figure 6B:
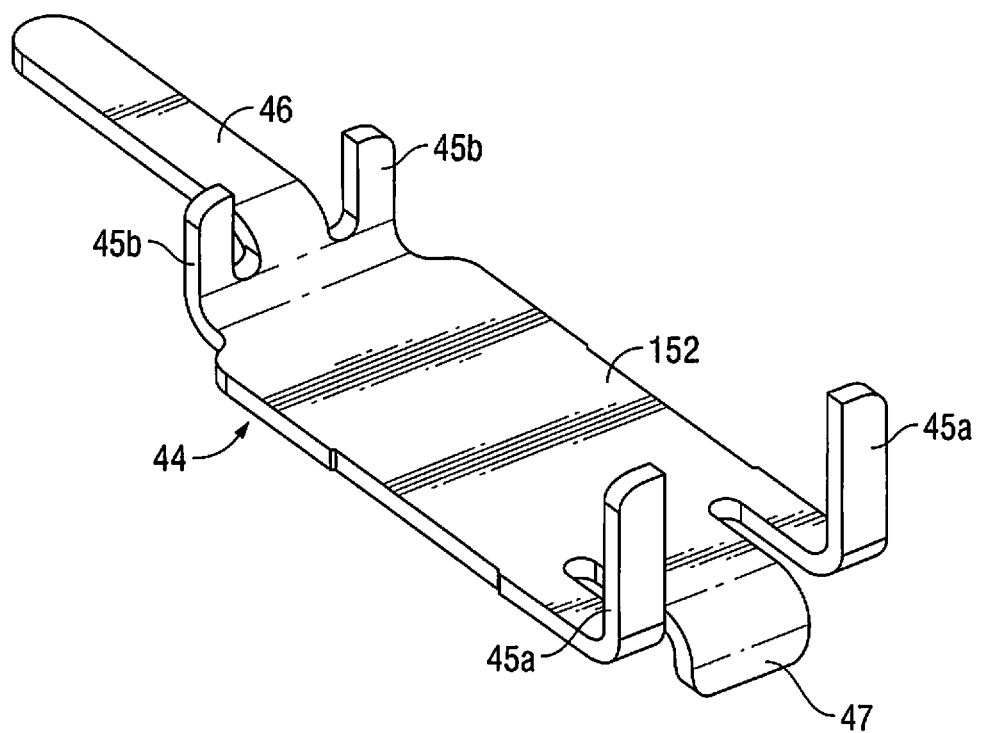
FIG. 6B is a perspective view of the safety plate of the firing lockout mechanism.

When the rotation knob 22 is rotated to approximate the anvil assembly 30, screw 40 with connected screw stop 49 moves proximally to urge safety plate 44 (FIG. 6B) of the lockout mechanism proximally against the bias of a spring 42 positioned on proximal extension 46 (FIG. 6B) of safety plate 44. That is, as screw stop 49 moves proximally, extending tab portion or engagement member 48 of screw stop 49 (FIG. 6A) engages distal legs 45a of safety plate 44 to move safety plate 44 proximally to a position in which tab (down turned lip portion) 47 is spaced proximally and out of engagement with the upper surface of trigger lock 50 to permit pivoting of trigger lock 50 in the direction of arrow "B" in FIG. 5 to an enabling position, thereby enabling firing of surgical stapling instrument 10.

Figure 4B:
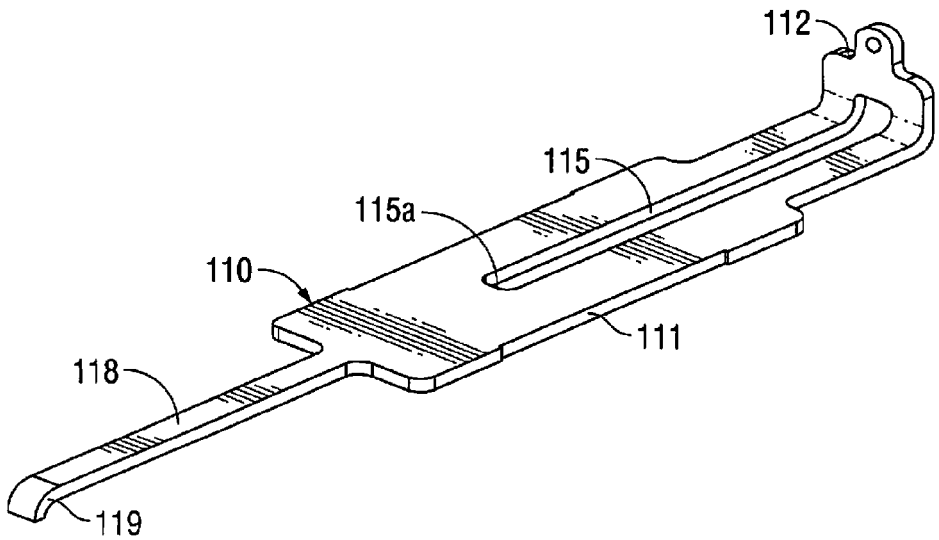
FIG. 4B is a perspective view of the slide member for the indicator mechanism.

As shown in FIGS. 4 and 5, indicator mechanism 100 of the present disclosure includes a bulbous indicator 102, lens cover 104 and a slide member 110. Slide member 110 (FIG. 4B) includes body portion 111 having an elongated slot 115, a distal abutment member or upturned lip portion 112 and a proximal extension 118. Indicator 102 is pivotally supported via pin 109 on projecting portion 112 of slide member 110 which may be formed monolithically with handle assembly 12. Lens cover 104 (or window of handle assembly 12) is positioned above indicator 102 and may be formed of magnification material to facilitate easy visualization of indicator 102. Slide member 110 is slidably positioned within handle assembly 12. A biasing member, e.g., a coil spring 120, is positioned about extension 118 and is configured to urge slide member 110 distally within stationary handle 18.

In the unapproximated (spaced) and unfired position of instrument 10 (FIGS. 1 and 4), biasing member 120 urges slide member 110 distally to maintain indicator 102 in a first position, which provides indication to a surgeon that the instrument 10 has not been approximated and is not in a fire-ready condition (see FIGS. 1 and 4).

Figure 4C:
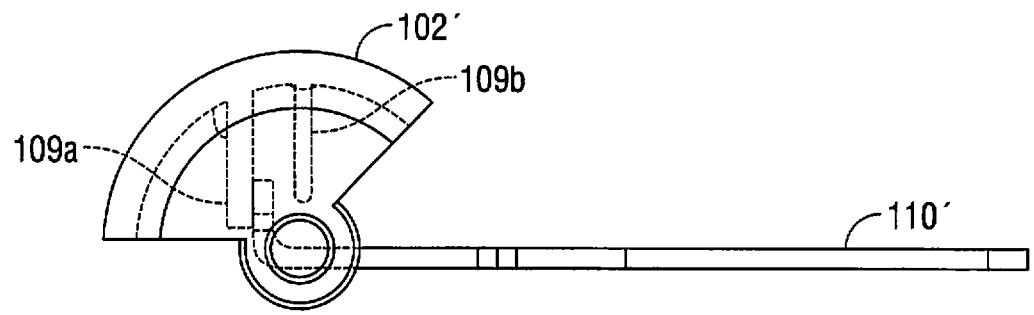
FIG. 4C is a side view of an alternate embodiment of the indicator mechanism.
Figure 4D:
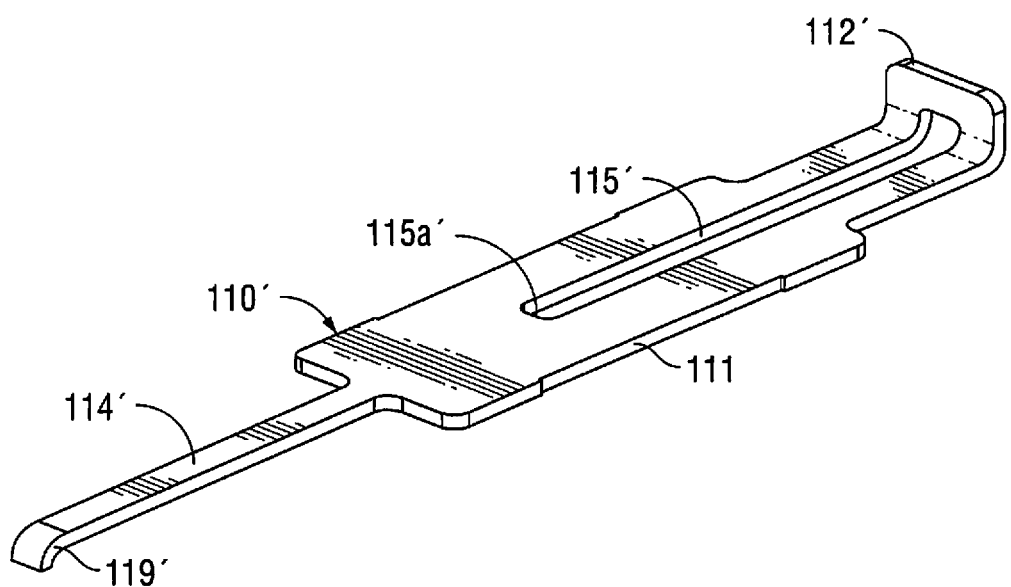
FIG. 4D is a perspective view of an alternate embodiment of the slide member for the indicator mechanism.

In an alternative embodiment, rather than the indicator attached to the pivot member (slide member) by a pin extending through the opening in lip portion 112, the projecting portion 112 engages an inner surface of the indicator. This is shown in the alternate embodiment of FIGS. 4C and 4D, wherein corresponding components are labeled with prime designations. Slide member 110' has a projecting portion or upturned lip portion 112' which abuts projections 103a, 103b of the indicator 102'. When slide member 110' is moved proximally upon approximation against the bias of the spring, portion 112' engages projection 103b causing indicator 102' to pivot. The engagement of the projecting portion 112 with projection 103b maintains the indicator in the first position.

With specific reference to FIGS. 4-5, during approximation of anvil assembly 30 and shell assembly 31, a tab 41 of screw stop 49 passes through slot 115 of slide member 110 and engages a proximal end 115a of the slot 115. Upon continued approximation of instrument 10, screw stop 49, due to contact of tab 41 with the proximal end 115a of slot 115, moves slide member 110 proximally within stationary handle 18 against the bias of spring 120 such that indicator 102 is rotated due to the pin attachment. In an alternative embodiment where the indicator is not pinned, e.g. the embodiment of FIGS. 4C and 4D, the projecting portion (upstanding lip) 112' of slide member 110' engages a portion, e.g. projection 103b, of indicator 102' causing indicator 102' to pivot (or rotate) to a second position. In the second position, indicator 102 (or 102') provides indication to a surgeon that the instrument has been approximated and is now in a fire-ready position (see FIGS. 2 and 5).

Actuation of firing trigger 20 (i.e., pivoting in the direction of arrow "A" in FIG. 1), to its actuated (fired) position, causes staples to be ejected from shell assembly 31 towards anvil assembly 30. That is, firing trigger 20 is disposed in mechanical cooperation with a pusher (not explicitly shown in the illustrated embodiments), such that actuation of firing trigger 20 causes advancement of the pusher into contact with the staples, which ejects the staples into staple deforming pockets of anvil assembly 130. More specifically, when firing trigger 20 is actuated, i.e. pivoted about pivot member 29, firing link 27 is moved proximally. Firing trigger 20 is moved distally to advance a pusher link 26 distally against its spring bias. The distal end of pusher link 26, attached to a pusher back (not shown), advances the pusher back to eject the staples from the shell assembly 31. Details of the firing mechanism and indicator mechanism are described in U.S. Pat. No. 7,303,106, incorporated by reference herein in its entirety.

Figure 7:
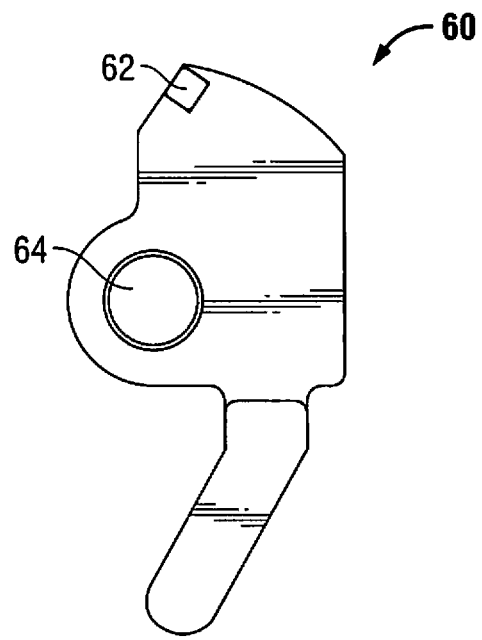
FIG. 7 is a side view of a pawl of the surgical stapling instrument of FIGS. 1-6.

Referring now to FIGS. 5 and 6, a complete actuation (complete firing stroke) of firing trigger 20 causes indicator 102 to pivot (or rotate) from its second position to its third position. Specifically, once firing trigger 20 is completely actuated (after approximation of the anvil assembly and release of the trigger lock 50), a tab 23 disposed on firing trigger 20 contacts a pawl 60 disposed in mechanical cooperation (e.g., pivotable or rotatable about an aperture 64 (see FIG. 7) with stationary handle 18. The engagement between tab 23 and pawl 60 causes pawl 60 to rotate in the general direction of arrow "C" in FIG. 6. As pawl 60 rotates, a rib 62 (FIG. 7) of pawl 60 contacts an extension 119 (FIG. 4B) of slide member 110, causing proximal translation of slide member 110. As slide member 110 translates proximally, its mechanical engagement with indicator 102 via pin 109 in one embodiment (e.g. FIG. 4B) and inner surface abutment with projection 103 in an alternate embodiment (e.g. FIGS. 4C and 4D), causes indicator 102 to move (pivot) to a third position. In the third position, indicator 102 provides indication to a surgeon that the instrument has been fired (see FIGS. 3 and 6).

Figure 8:
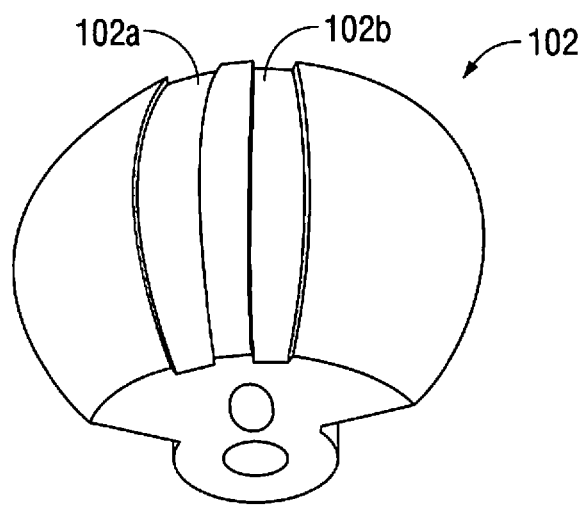
FIG. 8 is a perspective view of an indicator of the surgical stapling instrument of FIGS. 1-6.

With reference to FIG. 8, it is envisioned that indicator 102 includes indicia thereon to help a user determine the clamping/firing status of surgical stapling instrument 10. For example, indicator 102 can include a first color strip 102a of a first color which is visible to a user when indicator 102 is in its second position, and a second color strip 102b of a second color which is visible to the user when indicator 102 is in its third position. Indicator 102 may include other indicia (e.g., words, letters, bumps, etc.) thereon. Further, indicator 102 may include a third indicia thereon, for example, to show when indicator 102 is in its first, pre-approximated and non-fired position.

Further details of other features of surgical instrument 10, such as the approximation assembly, firing assembly, lock out mechanism and indicator mechanism are disclosed in commonly-owned U.S. Pat. Nos. 7,168,604 and 7,303,106, the entire contents of each of which are incorporated by reference herein.

The present disclosure also relates to a method of performing a surgical procedure. The method includes providing a surgical instrument 10 including a handle assembly, 12, an elongated body portion 14 extending distally from handle assembly 12, a head portion 16 and an indicator mechanism 100. Handle assembly 12 includes a firing trigger 20, which is movable between a first non-actuated position and a second actuated position. Head portion 16 is disposed adjacent a distal portion of the elongated body portion 14 and includes an anvil assembly 30 and a shell assembly 31. Anvil assembly 30 is movable in relation to shell assembly 31 between spaced and approximated positions. An indicator 102 of indicator mechanism 100 is disposed in mechanical cooperation with handle assembly 12. The method also includes the steps of positioning the surgical instrument 10 adjacent a surgical site, moving the anvil assembly 30 towards its approximated position to move the indicator 102 from a first position to a second position, and moving the firing trigger 20 through a firing stroke, preferably a complete firing stroke, to move the indicator 102 from the second to a third position.

It will be understood that various modifications may be made to the embodiments disclosed herein. Therefore, the above description should not be construed as limiting, but merely as exemplifications of disclosed embodiments. Those skilled in the art will envision other modifications within the scope and spirit of the claims appended hereto.

What is claimed:

1. A method of performing a surgical task, the method comprising:
   providing a surgical instrument comprising:
      a handle assembly;
      an elongated body portion extending distally from the handle assembly;
      first and second jaw members disposed adjacent a distal portion of the elongated body portion, the first jaw member supporting an anvil assembly and the second jaw member supporting a shell assembly, the shell assembly including a circular array of staples; and
      an indicator disposed in mechanical cooperation with the handle assembly;
   moving the first jaw member toward the second jaw member to move the indicator from a first position toward a second position; and
   firing the surgical instrument, while maintaining the first jaw member fixed in relation to the second jaw member, to eject the circular array of staples from the shell assembly and to move the indicator from the second position toward a third position.

2. The method of claim 1, wherein the indicator comprises at least two different indicia including a first indicia being visible to a user when the indicator is in the second position and a second indicia being visible to the user when the indicator is in the third position.

3. The method of claim 1, wherein the indicator rotates in a first direction from the first position toward the second position, and wherein the indicator rotates in the first direction from the second position toward the third position.

4. The method of claim 1, further comprising a slide member operatively associated with the indicator, and further comprising an approximation mechanism for moving the first jaw member towards the second jaw member, the approximation mechanism including a screw stop engageable with the slide member to move the slide member proximally upon retraction of the screw stop to move the indicator to the second position.

5. The method of claim 1, further comprising a lockout mechanism disposed in mechanical cooperation with the handle assembly, wherein movement of the first jaw member towards the second jaw member causes the lockout mechanism to move from a blocking position towards an enabling position.

6. The method of claim 1, wherein firing the surgical instrument includes causing fasteners to be ejected from one of the jaw members toward the other jaw member.

7. A method of surgical joining tissue, the method comprising:
   providing a surgical instrument comprising:
      a handle assembly including a movable handle;
      an elongated body portion extending distally from the handle assembly;
      first and second jaw members disposed adjacent a distal portion of the elongated body portion, the first jaw member being movable with respect to the second jaw member between spaced and approximated position, the first jaw member supporting an anvil assembly and the second jaw member supporting a shell assembly, the shell assembly including a circular array of staples; and
      an indicator disposed in mechanical cooperation with the handle assembly;
   actuating the movable handle to a first predetermined position to move the first jaw member in relation to the second jaw member from the spaced position to the approximated position to move the indicator from a first position to a second position; and
   actuating the movable handle from the first predetermined position to a second predetermined position to eject the circular array of staples from the shell assembly and to move the indicator from the second position to a third position.

8. The method of claim 7, wherein the handle assembly includes a pawl and wherein the movable handle is configured to contact the pawl when the movable handle is moved to the second predetermined position.

9. The method of claim 8, wherein the handle includes a stationary handle, and wherein the indicator is rotatable with respect to the stationary handle in a first direction.

10. The method of claim 9, wherein the pawl is rotatable relative to the stationary handle in a second direction, the second direction being different from the first direction.

11. The method of claim 7, wherein the indicator includes at least two different indicia including a first indicia being visible to a user when the indicator is in its second position and a second indicia being visible to the user when the indicator is in its third position.

12. The method of claim 7, wherein the handle assembly includes a window, and wherein a portion of the indicator is viewable through the window.

13. The method of claim 7, wherein the indicator is biased towards its first position.

14. The method of claim 7, wherein the indicator rotates in a first direction from the first position toward the second position, and wherein the indicator rotates in the first direction from the second position toward the third position.

15. The method of claim 7, wherein the elongated body portion includes a longitudinally curved portion.

16. The method of claim 7, further comprising a slide member operatively associated with the indicator and an approximation mechanism for moving the first jaw member between spaced and approximated positions, the approximation mechanism including a screw stop engageable with the slide member to move the slide member proximally upon retraction of the screw stop to move the indicator to the second position.

17. The method of claim 7, further comprising a lockout mechanism disposed in mechanical cooperation with the handle assembly, wherein approximation of the jaw members causes the lockout mechanism to move from a blocking position where the movable handle is prevented from moving toward a stationary handle, to an enabling position where the movable handle is capable of moving toward the stationary handle.

18. A method of surgical joining tissue, the method comprising:
 providing a surgical instrument comprising:
  a handle assembly including a movable handle and a pawl and wherein the movable handle is configured to contact the pawl when the movable handle is moved to the second predetermined position;
  an elongated body portion extending distally from the handle assembly;
  first and second jaw members disposed adjacent a distal portion of the elongated body portion, the first jaw member being movable with respect to the second jaw member between spaced and approximated position;
  an indicator disposed in mechanical cooperation with the handle assembly; and
 actuating the movable handle to a first predetermined position such that the indicator moves from a first position to a second position; and
 actuating the movable handle from the first predetermined position to a second predetermined position such that the indicator moves from the second position to a third position,
  the surgical instrument further comprising a slide member operatively associated with the indicator, the pawl including an engagement surface engageable with the slide member to effect further proximal movement of the slide member to move the indicator to the third position.

19. A method of surgical joining tissue, the method comprising:
 providing a surgical instrument comprising:
  a handle assembly including a movable handle and a pawl and wherein the movable handle is configured to contact the pawl when the movable handle is moved to the second predetermined position;
  an elongated body portion extending distally from the handle assembly;
  first and second jaw members disposed adjacent a distal portion of the elongated body portion, the first jaw member being movable with respect to the second jaw member between spaced and approximated position;
  an indicator disposed in mechanical cooperation with the handle assembly; and
 actuating the movable handle to a first predetermined position such that the indicator moves from a first position to a second position; and
 actuating the movable handle from the first predetermined position to a second predetermined position such that the indicator moves from the second position to a third position,
  the surgical instrument further comprising a slide member operatively associated with the indicator, the pawl having an engagement surface engageable with the slide member to retract the slide member.

20. A method of surgical joining tissue, the method comprising:
 providing a surgical instrument comprising:
  a handle assembly including a movable handle;
  an elongated body portion extending distally from the handle assembly;
  first and second jaw members disposed adjacent a distal portion of the elongated body portion, the first jaw member being movable with respect to the second jaw member between spaced and approximated position;
  an indicator disposed in mechanical cooperation with the handle assembly; and
 actuating the movable handle to a first predetermined position such that the indicator moves from a first position to a second position; and
 actuating the movable handle from the first predetermined position to a second predetermined position such that the indicator moves from the second position to a third position,
  the surgical instrument further comprising a slide member operatively associated with the indicator and an approximation mechanism for moving the first jaw member between spaced and approximated positions, the approximation mechanism including a screw stop engageable with the slide member to move the slide member proximally upon retraction of the screw stop to move the indicator to the second position, wherein the handle assembly includes a pawl and the movable handle is configured to contact the pawl when the movable handle has moved to its second predetermined position, the pawl having an engagement surface engageable with the slide member to move the slide member farther proximally to move the indicator to the third position.

* * * * *